United States Patent
Lin

(10) Patent No.: US 6,450,993 B1
(45) Date of Patent: Sep. 17, 2002

(54) HALF-DISPOSABLE SYRINGE BARREL

(76) Inventor: Bih-Chern Lin, 7F-3, No. 2, Lane 222, Jin-Long Rd., Ney-Hwa Dist., Taipei (TW)

( * ) Notice: Subject to any disclaimer, the term of this patent is extended or adjusted under 35 U.S.C. 154(b) by 0 days.

(21) Appl. No.: 09/438,520

(22) Filed: Nov. 12, 1999

(51) Int. Cl.[7] ................................................ A61M 1/00
(52) U.S. Cl. ..................................................... 604/199
(58) Field of Search ................................ 604/187, 188, 604/190, 191, 192, 199, 200, 212, 218, 221, 222

(56) References Cited

U.S. PATENT DOCUMENTS 6,142,976 A * 11/2000 Kubo .......................... 604/199

* cited by examiner

Primary Examiner—Anhtuan T. Nguyen
Assistant Examiner—Ann Y. Lam
(74) Attorney, Agent, or Firm—Bacon & Thomas, PLLC

(57) ABSTRACT

A Half-disposable syringe barrel including a barrel syringe and a cap member as two stages. A plunger is fitted in the syringe barrel. An emulsion ring is disposed in the cap member. The emulsion ring is formed with a membrane and is made of highly flexible material. A lubricant is overlaid on the emulsion ring and the membrane thereof. The cap member is fitted with the front end of the syringe barrel. When pulling the plunger backward to suck a medicine, the highly flexible membrane of the emulsion ring is extended and sucked to attach to the wall of the syringe barrel. Therefore, the medicine is enclosed by the emulsion ring and the membrane and isolated from the wall of the syringe barrel. Therefore, the syringe barrel and the plunger are not contaminated by the medicine and the flowing back blood. After the cap member is removed, the syringe barrel can be recovered for reuse.

7 Claims, 5 Drawing Sheets

HALF-DISPOSABLE SYRINGE BARREL

BACKGROUND OF THE INVENTION

The present invention relates to a half-disposable syringe barrel which is able to isolate the syringe barrel from the medicine and the flowing back blood and prevent the syringe barrel from being contaminated thereby. The syringe barrel is applicable to the injection syringes used in various hospitals and clinics.

In the existent hospitals or clinics, injections are taken quite frequently during therapy. Some of the syringe barrels are discarded after used. However, some syringe barrels are made of glass. After injection, the needle is extracted and the glass syringe barrel is sterilized for re-use. Although the amount of medical waste can be reduced by such procedure, the sterilization may be incomplete to lead to infection.

In order to ensure that the patient is protected from being injected with the infected glass syringe barrel, the plastic-made syringe barrel is used instead of the glass-made one. The plastic syringe barrel is discarded after used without repeated use. This ensures the safety of the patient. However, a great amount of medical wastes are produced due to the disposable syringe barrel. It is troublesome to treat these medical wastes and resource is wasted. In fact, the needle of the syringe, which is surely contaminated, should be detached from the syringe barrel and discarded without further use, while the syringe barrel which is not contaminated can be recovered and the material can be used for reproduction to save resource.

SUMMARY OF THE INVENTION

It is therefore a primary object of the present invention to provide a half-disposable syringe barrel which is able to isolate the syringe barrel from the medicine and the flowing back blood and prevent the syringe barrel from being contaminated thereby.

It is a further object of the present invention to provide the above half-disposable syringe barrel which permits effective recovery of medical resource and reduces the amount of medical waste.

According to the above objects, the half-disposable syringe barrel of the present invention includes a barrel syringe and a cap member as two stages. A plunger is fitted in the syringe barrel. An emulsion ring is disposed in the cap member. The emulsion ring is formed with a membrane and is made of highly flexible material. A lubricant is overlaid on the emulsion ring and the membrane thereof. The cap member is fitted with the front end of the syringe barrel. When pulling the plunger backward to suck a medicine, the highly flexible membrane of the emulsion ring is extended and sucked to attach to the wall of the syringe barrel. Therefore, the medicine is enclosed by the emulsion ring and the membrane and isolated from the wall of the syringe barrel. Therefore, the syringe barrel and the plunger are not contaminated by the medicine and the flowing back blood. After the cap member is removed, the syringe barrel can be recovered for reuse.

The present invention can be best understood through the following description and accompanying drawings wherein:

DETAILED DESCRIPTION OF THE PREFERRED EMBODIMENT

Figure 1:
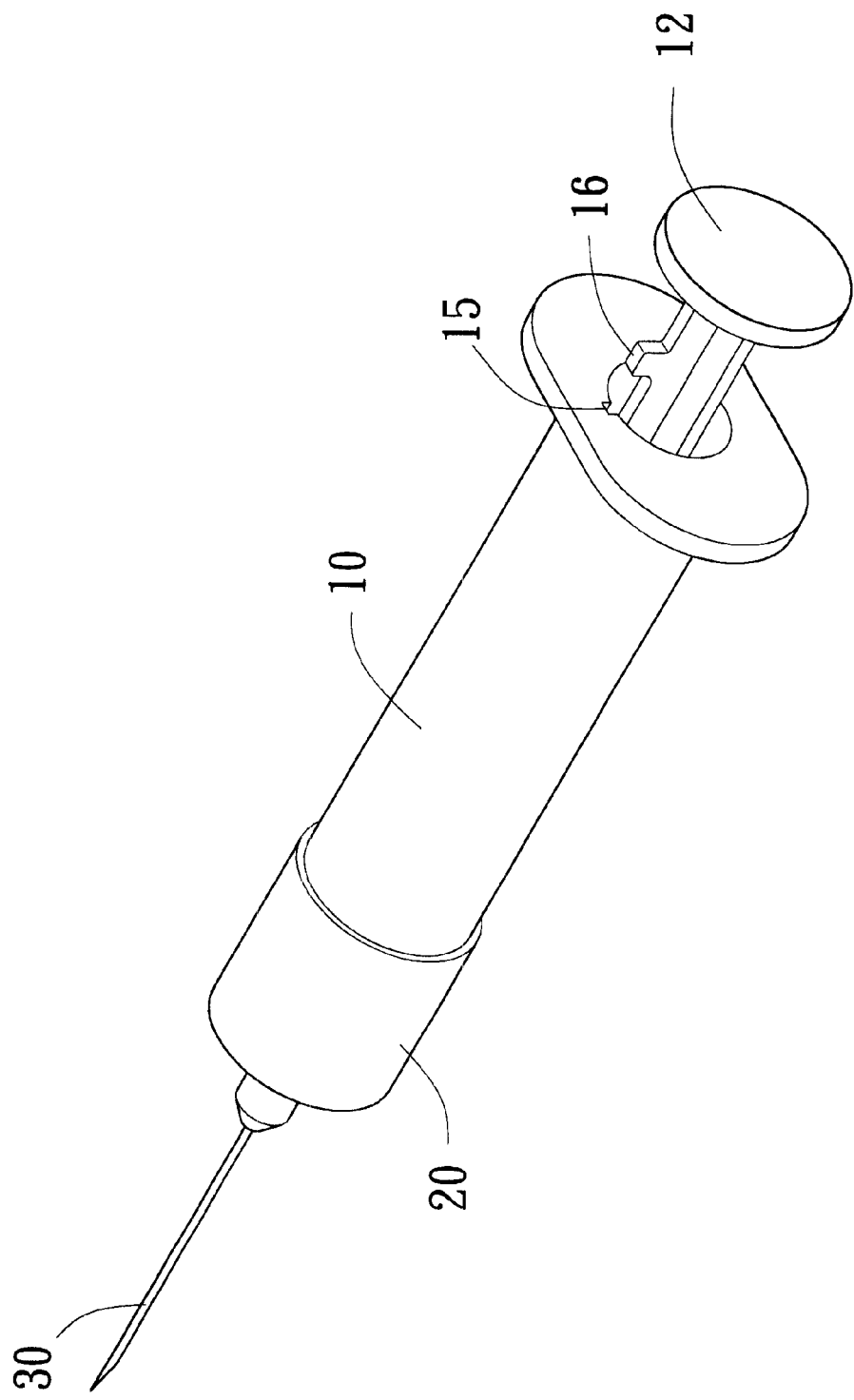
FIG. 1 is a perspective assembled view of the present invention.

Please refer to FIG. 1. The half-disposable syringe barrel of the present invention is composed of a syringe barrel 10 and a cap member 20.

Figure 2:
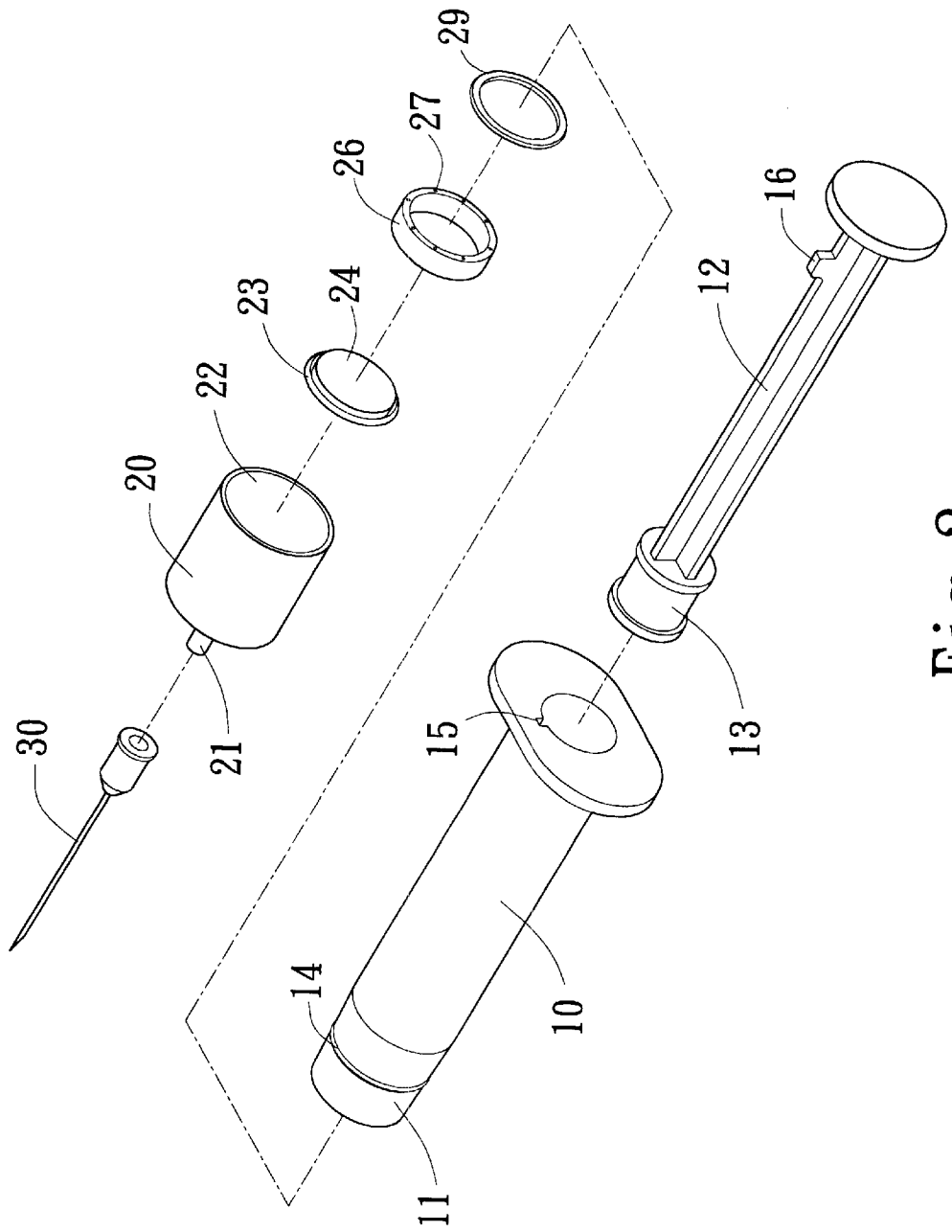
FIG. 2 is a perspective exploded view of the present invention.

Referring to FIG. 2, the syringe barrel 10 is a hollow tubular body. The front end thereof is a conic opening section 11. The outer circumference of the opening section 11 is formed with an annular rib 14. The rear end of the syringe barrel 10 is formed with a notch 15. A plunger 12 is fitted into the syringe barrel 10. The front end of the plunger 12 is disposed with a rubber ring 13. The rear end of the plunger 12 is formed with a protuberance 16.

The opening 22 of the cap member 20 is slightly larger than the base thereof so that the cap member 20 as a whole has a substantially conic profile. The inner wall face of the cap member 22 is formed with an annular groove 28. The base of the cap member 20 is formed with a needle holder 21 for fitting with an injection needle 30. An emulsion ring 23 integrally formed with a membrane 24 is fitted onto the base of the cap member 20. The emulsion ring 23 is made of highly flexible material. A layer of lubricant 25 is overlaid on the emulsion ring 23 and the membrane 24. A ventilation ring 26 is further placed onto the emulsion ring 23 and the membrane 24. The peripheral wall of the ventilation ring 26 is formed with multiple vents 27. An O-ring 29 is further fitted onto rear side of the ventilation ring 26. When packed, the opening 22 of the cap member 20 is sealed by a sealing layer.

Figure 3:
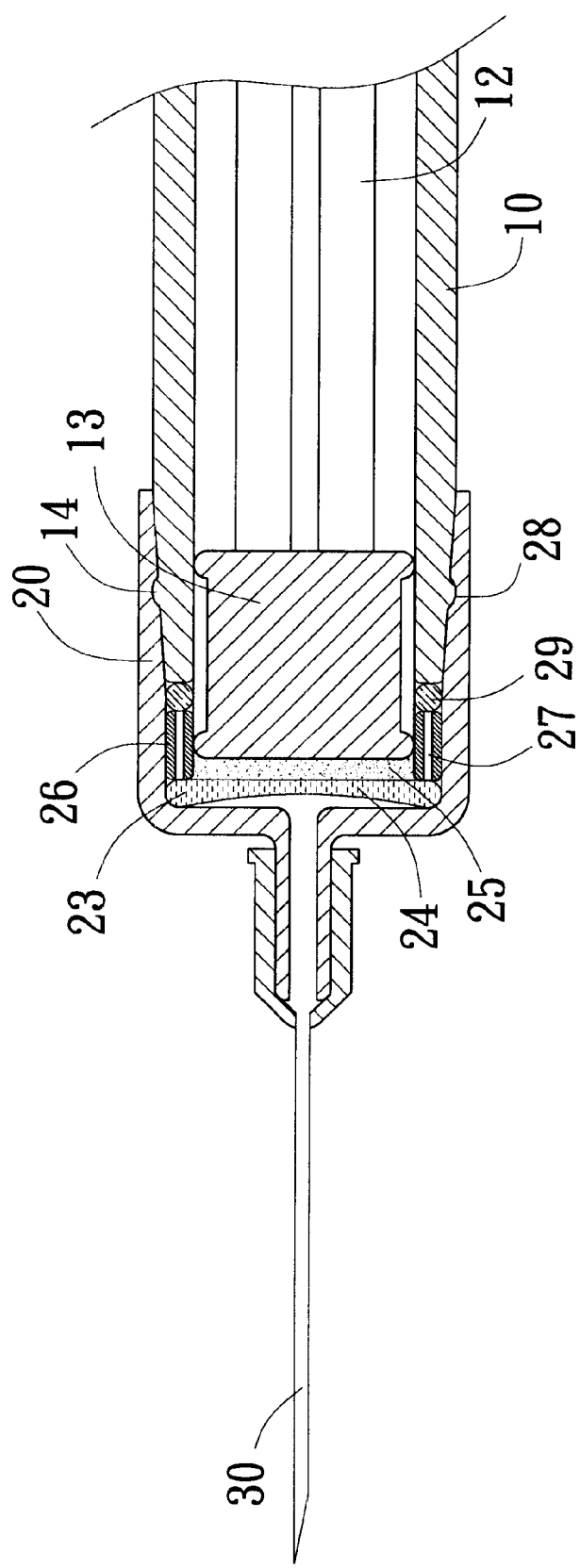
FIG. 3 is a sectional view of the present invention.
Figure 4:
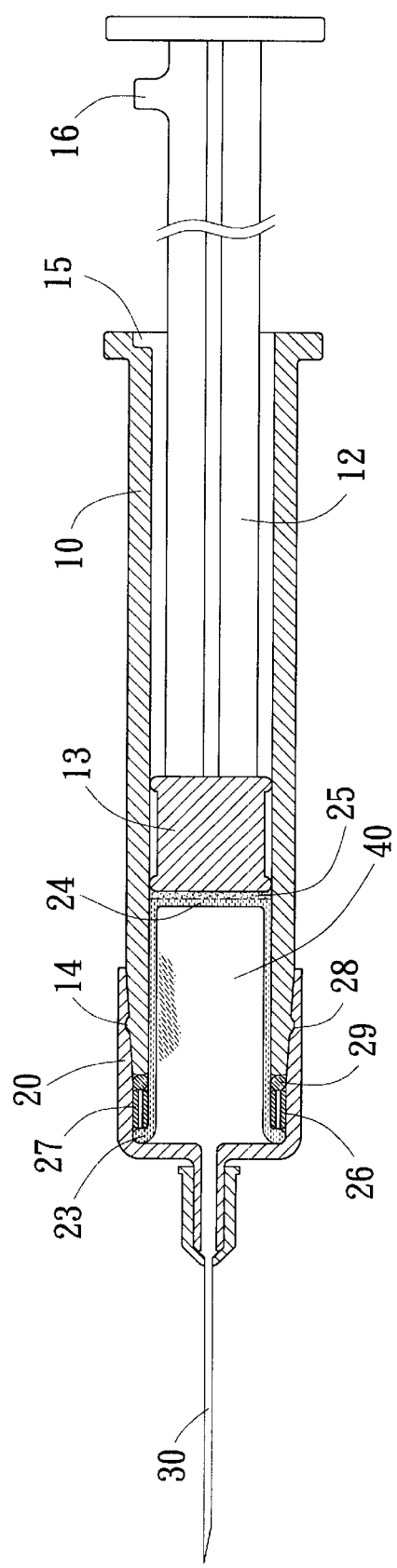
FIG. 4 is a sectional view showing the use of the present invention.

Referring to FIGS. 3 and 4, in use, the sealing layer of the cap member 20 is first torn away and the opening section 11 of the syringe barrel 10 is directly placed into the cap member 20. At this time, the annular rib 14 of the opening section 11 is engaged into the annular groove 28 of the inner wall face of the opening 22 of the cap member 20, whereby the front end of the syringe barrel 10 tightly abuts against the O-ring 29, ventilation ring 26 and emulsion ring 23. Accordingly, the syringe barrel 10 is connected with the cap member 20 not only by means of the coning, but also by means of the annular rib and annular groove. Therefore, the syringe barrel 10 and the cap member 20 are double firmly engaged with each other to reduce void.

During the connection of the syringe barrel 10 and the cap member 20, in the case that air is contained in the syringe barrel 10, the plunger 12 is pressed to the bottom so as to make the air escape through the vents 27 of the ventilation ring 26 and vacuumize the space between the rubber ring 13 and the emulsion ring 23. After the injection needle 30 is thrust into the medicine bottle, the plunger 12 is pulled backward. At this time, the rubber ring 13 is lubricated by the lubricant 25 and can be easily pulled or pushed. In addition, the membrane 24 of the emulsion ring 23 has high flexibility so that when the plunger 12 and the rubber ring 13 are pulled backward, the membrane 24 is extended and sucked to attach to the wall of the syringe barrel 10. After the medicine 40 is guided into syringe barrel 10 through the injection needle 30, the medicine is enclosed by the emulsion ring 23 and the membrane 24 and isolated from the wall of the syringe barrel 10 and the rubber ring 13. Therefore, the syringe barrel 10 and the plunger rubber ring 13 are totally not contaminated by the medicine 40.

Figure 5:
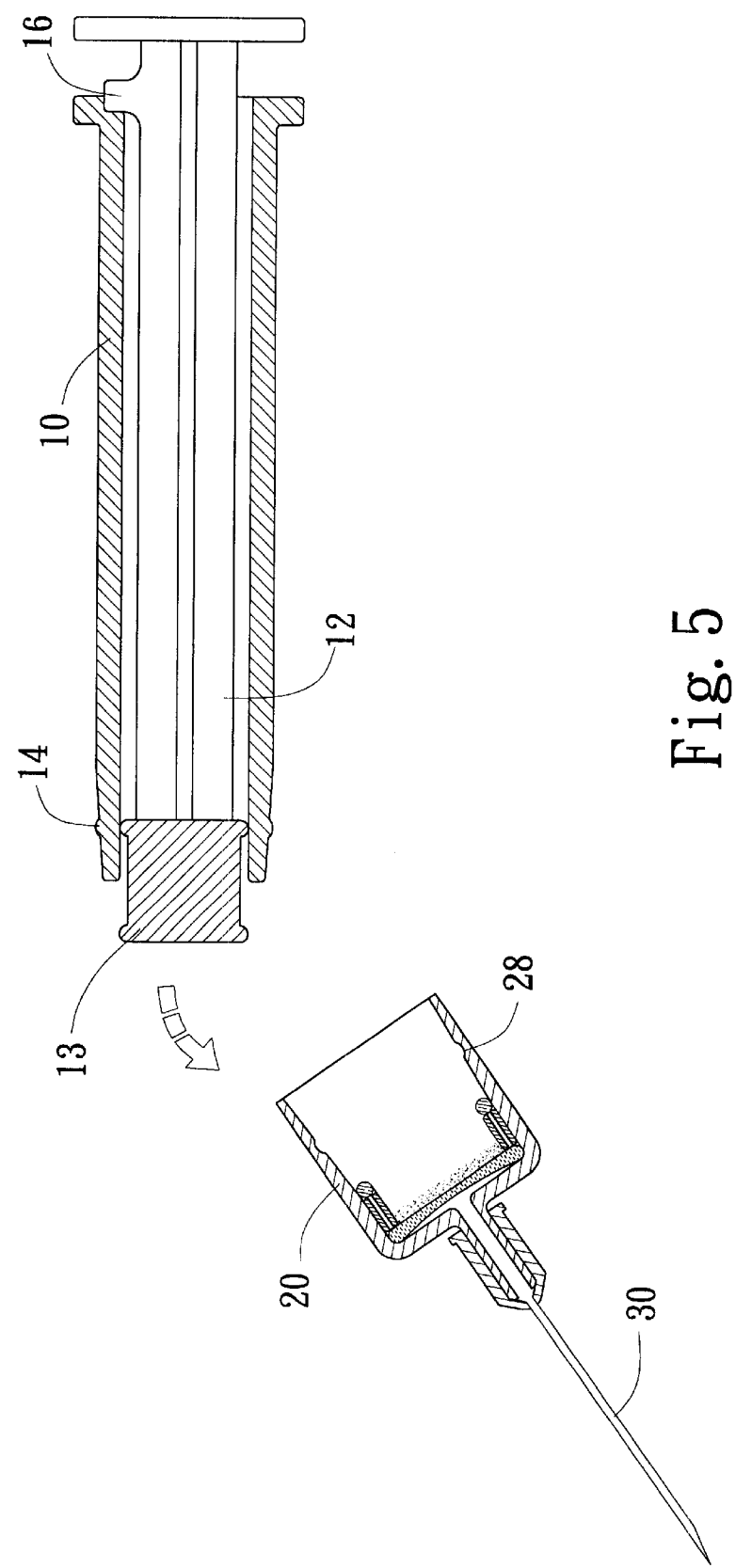
FIG. 5 is a sectional view showing that the cap member is separated from the syringe barrel.

Referring to FIG. 5, after the injection is completed, since the injection needle 30 has contacted with the patient and the emulsion ring 23 and membrane 24 in the cap member 20 have been contaminated by the medicine, the cap member 20 needs to be separated and discarded. At this time, a user only needs to rotate the plunger 12 to align the protuberance 16 thereof with the notch 15 of the rear end of the syringe barrel 10 and then press the plunger 12 to the bottom to make the rubber ring 13 forcedly push the O-ring 29. At this time, the annular rib 14 of the front end of the syringe barrel 10 is disengaged from the annular groove 28 of the inner wall face of the opening 22 of the cap member 20. Under such circumstance, the cap member 20 can be separated from the syringe barrel 10. The syringe barrel 10 and the plunger 12 which are not contaminated by the medicine 40 can be sterilized and recovered for reuse so as to reduce the amount of medical waste.

According to the above arrangement, the half-disposable syringe barrel of the present invention can ensure the safety in use of the injection syringe as well as apparently reduce the amount of medical waste.

The above embodiment is only used to illustrate the present invention not intended to limit the scope thereof. Many modifications of the above embodiment can be made without departing from the spirit of the present invention.

What is claimed is:

1. A half-disposable syringe barrel comprising:

a syringe barrel which is a hollow tubular body in which a plunger is fitted;

a cap member in which an emulsion ring, a ventilation ring and an O-ring are disposed, the emulsion ring being formed with a membrane, the cap member being detachably fitted with front end of the syringe barrel, whereby when sucking a medicine, the emulsion ring and the membrane thereof form a protective film covering the wall of the syringe barrel to isolate the medicine and the wall of the syringe barrel, after used, the cap member being detached from the syringe barrel and discarded, while the syringe barrel and the plunger being recovered; and wherein the peripheral wall of the ventilation ring is formed with multiple vents through which the air in the syringe barrel escapes.

2. The half-disposable syringe barrel as claimed in claim 1, wherein the syringe barrel and the cap member have cooperative conic profiles for filing with each other by means of the coning.

3. The half-disposable syringe barrel as claimed in claim 1, wherein the syringe barrel and the cap member are formed with corresponding annular rib and annular groove for engaging with each other.

4. The half-disposable syringe barrel as claimed in 1, wherein the rear ends of the syringe barrel and the plunger are formed with corresponding notch and protuberance, whereby the protuberance is aligned with the notch, the syringe barrel can be separated from the cap member.

5. The half-disposable syringe barrel as claimed in claim 1, wherein the emulsion ring and the membrane thereof are made of highly flexible material.

6. The half-disposable syringe barrel as claimed in claim 1, wherein a lubricant is overlaid on the emulsion ring and the membrane thereof.

7. The half-disposable syringe barrel as claimed in claim 1, wherein the opening of the cap member is sealed by a sealing layer.

* * * * *